US00PP12060P2

(12) United States Plant Patent
Sanchez

(10) Patent No.: US PP12,060 P2
(45) Date of Patent: Aug. 14, 2001

(54) HOLLY PLANT NAMED 'HONEY MAID'

(76) Inventor: Angel M. Sanchez, 372 Rose Hill Rd., West Grove, PA (US) 19390

( * ) Notice: Subject to any disclaimer, the term of this patent is extended or adjusted under 35 U.S.C. 154(b) by 0 days.

(21) Appl. No.: 09/526,313

(22) Filed: Mar. 16, 2000

(51) Int. Cl.[7] ..... A01H 5/00
(52) U.S. Cl. ..... Plt./247
(58) Field of Search ..... Plt./247

*Primary Examiner*—Bruce R. Campell
*Assistant Examiner*—June Hwu

(57) ABSTRACT

A new and distinct Ilex variety is provided having multi-colored foliage which originated through the discovery of a branch mutation of unknown causation of the *Ilex*× *meserveae* 'Mesid' variety (U.S. Plant Pat. No. 4,685). The new variety exhibits attractive variegated dark green glossy foliage that is irregularly bordered with yellow and cream coloration. The plant is generally smaller than the 'Mesid' variety. The growth habit is dense, compact, well-branched, and vigorous. Semi-glossy red berries are formed. Good winter hardiness is exhibited.

2 Drawing Sheets

SUMMARY OF THE INVENTION

The parent 'Mesid' variety (U.S. Plant Pat. No. 4,685) was formed by crossing an *Ilex aquifolium* seedling and an *Ilex rugosa* seedling to form a plant that is botanically classified *Ilex*×*meserveae*. Such plant displays very glossy deep green leaves of substantially uniform coloration. The 'Mesid' variety is being marketed under the BLUE MAID trademark.

The new variety of the present invention was discovered during 1990 while present among one year-old rooted cuttings of the 'Mesid' variety being grown at West Grove, Pa. It was found that a portion of a single plant of the 'Mesid' variety displayed a distinctive variegated foliage coloration that was unlike the other foliage. Such plant has been carefully maintained and studied. Had it not been discovered and preserved it would have been lost to mankind.

It was found that the new variety of *Ilex*×*meserveae* of the present invention:

(a) Unlike the 'Mesid' variety exhibits variegated dark green glossy foliage that is irregularly bordered with yellow and cream coloration,
(b) Exhibits a dense, compact, well-branched and vigorous growth habit that results in a generally smaller plant size than the 'Mesid' variety,
(c) Forms semi-glossy red berries, and
(d) Exhibits good winter hardiness.

The yellow and cream coloration at the margins of the newly-formed foliage tends to be partially replaced by green coloration as the leaves mature. The leaf coloration retains a fresh appearance throughout the winter.

At five years of age a plant of the new variety commonly achieves a height of approximately four feet and a width of approximately three feet. At full maturity a plant of the new variety is expected to achieve a height of approximately six feet and a width of approximately four to five feet. This can be compared to a maximum height of approximately ten to twelve feet and a maximum width of eight to ten feet for the parent 'Mesid' variety.

The hardiness of the new variety has been confirmed by overwintering in containers above ground at West Grove, Pa. Accordingly, the plant is hardy to at least U.S.D.A. Hardiness Zone 6a. Such hardiness exceeds that of most varieties of *Ilex aquifolium*.

Asexual reproduction of the new variety by cuttings has been carried out at West Grove, Pa. It has been demonstrated that the unique combination of characteristics is stable and is well established and is transmitted to successive generations following such asexual propagation.

The new variety is well suited for growing as distinctive ornamentation in the landscape. It can be used for garden decoration and general landscape use.

The new variety of the present invention has been named the 'Honey Maid' variety.

BRIEF DESCRIPTION OF THE PHOTOGRAPHS

The accompanying photographs show as nearly true as it is reasonably possible to make the same, in a color illustration of this character, typical specimens of the new variety. The photographs were obtained during June 1999 at West Grove, Pa. The plants were reproduced from cuttings and were approximately five years of age.

DETAILED DESCRIPTION

Figure 1:
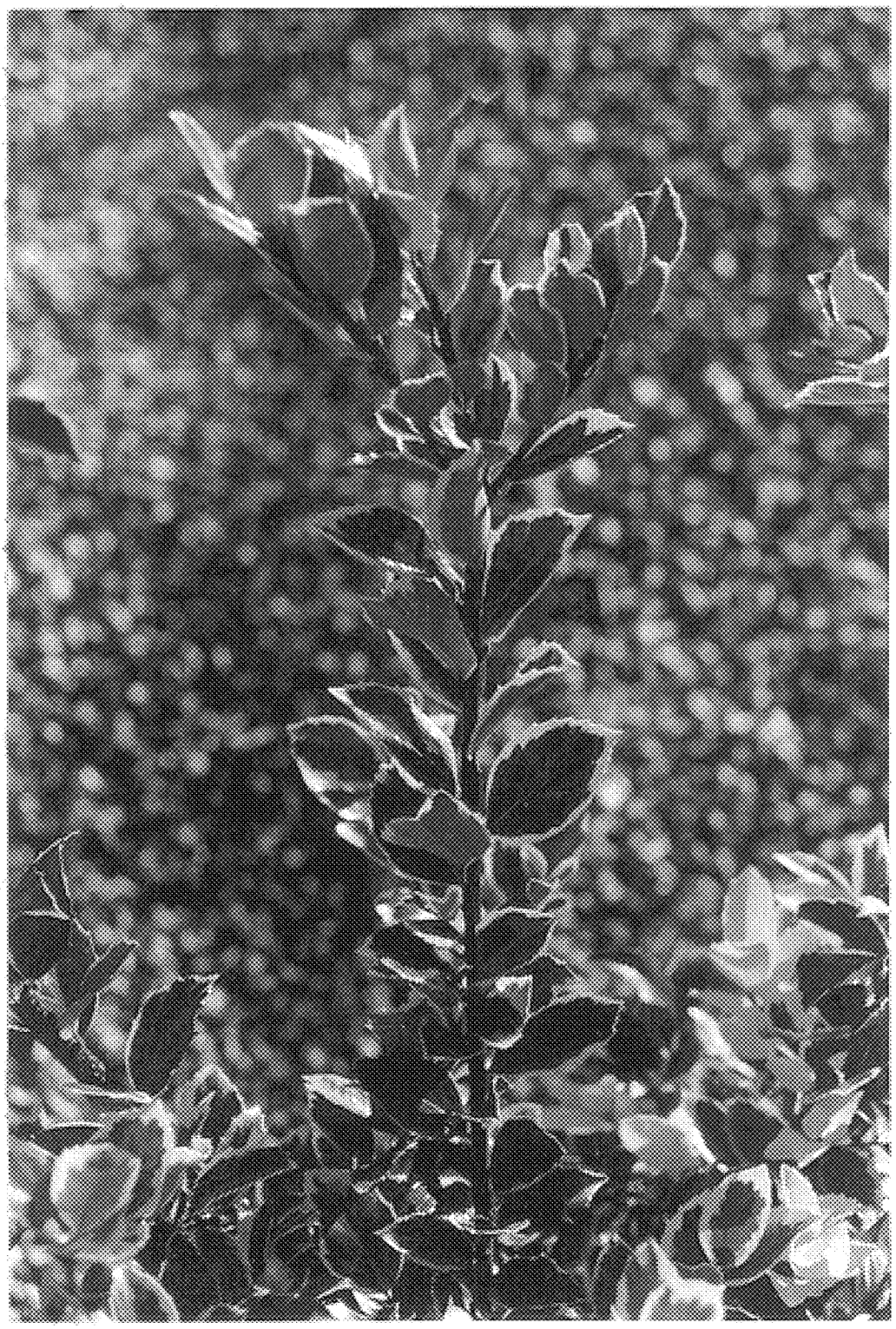
FIG. 1 illustrates a typical branch wherein the variegated foliage is shown.
Figure 2:
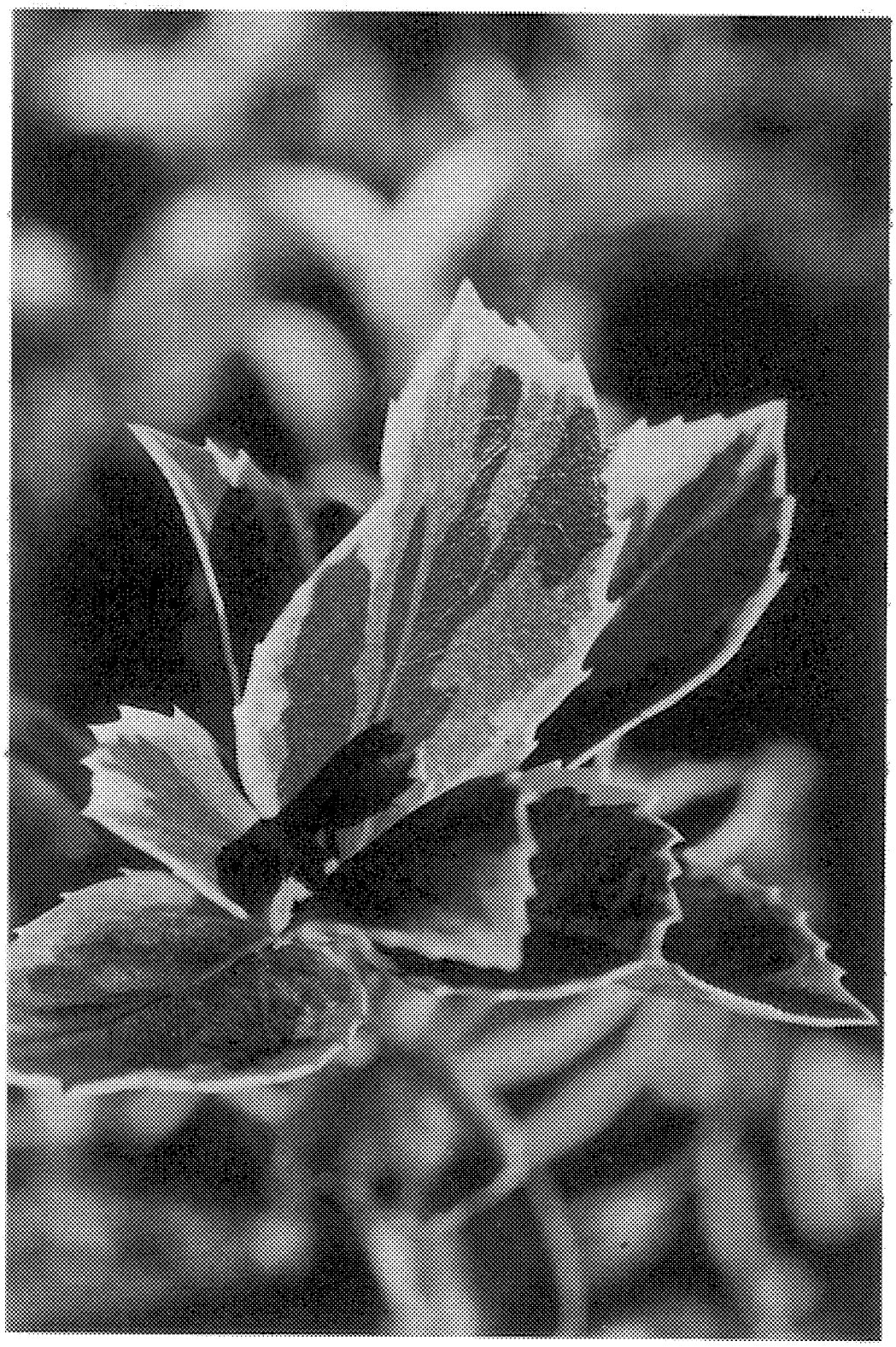
FIG. 2 illustrates a closer view of the variegated foliage of the new variety.

The following is a detailed description of the new variety of the present invention which was made from the observation of seven year-old plants being grown outdoors in containers at West Grove, Pa. Color terminology is in accordance with the R.H.S. Colour Chart of The Royal Horticultural Society, London. When common color terms are used they are to be accorded their ordinary dictionary significance.

Type: Hardy outdoor evergreen shrub for garden decoration and general landscape use.
Parentage: Sport of *Ilex aquifolium*×*Ilex rugosa*, 'Mesid' variety.
Botanical classification: *Ilex*×*meserveae*.
Foliage:
*Shape.*—Elliptic with an acuminate apex and an obtuse base.

*Margins.*—Serrate.

*Spines.*—Present on leaf margins. Leaves along the main stems of the current year's growth commonly possess approximately 9 to 12 spines, and leaves on the lateral branches of current year's growth commonly possess approximately 10 to 14 spines.

*Size.*—Mature leaves on main stems commonly are approximately 5 to 6 cm in length on average and approximately 2 to 3 cm in width on average.

*Petiole.*—Commonly approximately 0.5 cm in length. The upper side is yellowish-green (Yellow-Green Group 144B) and the under side is light green (a combination of Yellow-Green Group 149C and Yellow-Green Group 144C in coloration). The leaf arrangement is alternate.

*Juvenile leaves.*—Upper surface: Glossy and smooth with a blend of Greyed-Green Group 189A, Greyed-Green Group 191C and Green Group 139A, at the center, and a blend of Yellow Group 9B and Yellow-Orange Group 16D at the margins. Some light green venation, dorsal side Green Group 141C to 141D and ventral side Yellow-Green Group 145A to 145B, commonly is displayed. Under surface: Mattee and smooth with a blend of Greyed-Green Group 191A and Greyed-Green Group 191B at the center, and Yellow Group 13C at the margins.

*Mature leaves.*—Upper surface: Smooth with a blend of Greyed-Green Group 189A, Greyed-Green Group 189C, and Green Group 139A at the center, and a blend of Yellow Group 11A and Yellow-Orange Group 16D at the margins. Some light green venation, dorsal side Green Group 141C to 141D and ventral side Green Group 141C to 141D, commonly is displayed. Upper surface: Smooth with a blend of Greyed-Green Group 191A and Greyed-Green Group 191B at the center, and Yellow Group 10B at the margins.

*Young stems.*—Smooth, and Greyed-Purple Group 187A in coloration.

*Mature stems.*—Green Group 141D at the end of the stems and Yellow-White Group 158B below the end of the stems, with a slight pubescence.

*Mature lenticels.*—(3 years old stem) Oblong in shape, eruptive or protruding slightly above the surface. Average size 0.6 mm length×0.5 mm width, quantity of 50–60 lenticels per square inch, and the color White Group 155D to Greyed-White Group 156D.

*Immature lenticels.*—(1 year old stem) Oblong in shape, flushed with the surface. Average size 0.3 mm length×0.2 mm width, quantity of 15–20 lenticels per square inch, and the color Orange-White Group 159A.

Flowers:

*Bearing.*—Pistillate flowers are borne freely outdoors with several per stem in regular mounded clusters.

*Peduncle.*—Smooth, approximately 3 to 5 mm in length on average, light green, Yellow-Green Group 145C with a base of Greyed-Purple Group 185C.

*Calyx.*—2–3 mm diameter when flowers are fully opened. Texture under magnification minutely pebbled, otherwise through the naked eye smooth.

*Buds.*—Before the calyx breaks the flower buds are short, small, and globular without foliaceous appendages. As the calyx beaks, the initial petal coloration is Red Group 54C which changes to Red Group 56C as the flower continues to open.

*Open blooms.*—Single petalage with five petals that are relatively thin, soft and satiny on both surfaces. The blooms tend to be cupped and globular and approximately 6 mm in diameter. The upper petal surface is near White Group 155A with tips of Red Group 54C, and the under petal surface is near White Group 155B with tips of Red Group 54B. The blossom petals measure approximately 2 mm. The blossoms possess no fragrance. No male flowers are produced.

Berries:

*Size.*—Approximately 4 to 6 mm in diameter on average. The berries commonly persist on the plant from September through March. The seed color is Greyed-Yellow Group 161B to 161C, and the seeds are moderately ridged.

*General appearance.*—Semi-glossy and Red Group 43A in coloration.

Hardiness: Very good, overwinters well at West Grove, Pa.

Disease resistance: Good and generally comparable to that of its 'Mesid' variety parent. Resistance to Leaf Miner, Tar Spots (Hasidim) and Leaf Spot (Cerocospora) is exhibited.

I claim:

1. A new and distinct variety of *Ilex×meserveae* that originated as a spontaneous mutation of the 'Mesid' variety (U.S. Plant Pat. No. 4,685) having the following combination of characteristics:

(a) Unlike the 'Mesid' variety exhibits variegated dark green glossy foliage that is irregularly bordered with yellow and cream coloration, (b) Exhibits a dense, compact, well-branched and vigorous growth habit that results in a generally smaller plant size than the 'Mesid' variety, (c) Forms semi-glossy red berries, and (d) Exhibits good winter hardiness.

substantially as illustrated and described.

* * * * *

UNITED STATES PATENT AND TRADEMARK OFFICE

CERTIFICATE OF CORRECTION

PATENT NO. : PP 12,060 P2
DATED : August 14, 2001
INVENTOR(S) : Angel M. Sanchez It is certified that error appears in the above-identified patent and that said Letters Patent is hereby corrected as shown below:

Title page,
Please insert the following:

-- [73] Assignee: CP (DELAWARE) INC.
Wilmington, Delaware --

Signed and Sealed this

First Day of July, 2003

JAMES E. ROGAN
*Director of the United States Patent and Trademark Office*